US00PP22823P2

(12) United States Plant Patent
Beekenkamp

(10) Patent No.: US PP22,823 P2
(45) Date of Patent: Jun. 26, 2012

(54) ***DAHLIA* PLANT NAMED 'BKDAPOR'**

(50) Latin Name: *Dahlia hybrida*
Varietal Denomination: Bkdapor

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 13/065,473

(22) Filed: Mar. 22, 2011

(51) Int. Cl.
*A01H 5/00* (2006.01)

(52) U.S. Cl. ..... Plt./321

(58) Field of Classification Search ..... Plt./321
See application file for complete search history.

*Primary Examiner* — Kent L Bell
(74) *Attorney, Agent, or Firm* — C. A. Whealy

(57) ABSTRACT

A new and distinct cultivar of *Dahlia* plant named 'Bkdapor', characterized by its compact, upright, somewhat outwardly spreading and mounding plant habit; dense and bushy growth habit; early and continuous flowering habit; semi-double inflorescences with orange-colored ray florets and dark red-colored disc florets; and good garden performance.

2 Drawing Sheets

Botanical designation: *Dahlia hybrida.*
Cultivar denomination: 'BKDAPOR'.

BACKGROUND OF THE INVENTION

The present invention relates to a new and distinct cultivar of *Dahlia* plant, botanically known as *Dahlia hybrida* and hereinafter referred to by the name 'Bkdapor'.

The new *Dahlia* plant is a product of a planned breeding program conducted by the Inventor in Maasdijk, The Netherlands. The objective of the breeding program is to create new container *Dahlia* plants that have a freely branching habit, attractive ray floret coloration, long flowering period and good garden performance.

The new *Dahlia* plant originated from an open-pollination in June, 2006 in Maasdijk, The Netherlands of a proprietary selection of *Dahlia hybrida* identified as code number 2006-1000, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled environment in Maasdijk, The Netherlands in July, 2007.

Asexual reproduction of the new *Dahlia* plant by cuttings in a controlled environment in Maasdijk, The Netherlands since November, 2007 has shown that the unique features of this new *Dahlia* plant are stable and reproduced true to type in successive generations.

SUMMARY OF THE INVENTION

Plants of the new *Dahlia* have not been observed under all possible environmental conditions and cultural conditions. The phenotype may vary somewhat with variations in environment such as temperature and light intensity, without, however, any variance in genotype.

The following traits have been repeatedly observed and are determined to be the unique characteristics of 'Bkdapor'. These characteristics in combination distinguish 'Bkdapor' as a new and distinct *Dahlia* plant:

1. Compact, upright, somewhat outwardly spreading and mounding plant habit.

2. Dense and bushy growth habit.
3. Early and continuous flowering habit.
4. Semi-double inflorescences with orange-colored ray florets and dark red-colored disc florets.
5. Good garden performance.

Compared to plants of the female parent selection, plants of the new *Dahlia* differ primarily in the following characteristics:

1. Plants of the new *Dahlia* are more compact than plants of the female parent selection.
2. Plants of the new *Dahlia* have smaller inflorescences than plants of the female parent selection.
3. Plants of the new *Dahlia* and the female parent selection differ in ray floret color as plants of the female parent selection have orange red-colored ray florets.

Plants of the new *Dahlia* can be compared to plants of *Dahlia* 'Dahlstar Orange', not patented. In side-by-side comparisons conducted in Maasdijk, The Netherlands, plants of the new *Dahlia* differed from plants of 'Dahlstar Orange' in the following characteristics:

1. Plants of the new *Dahlia* and 'Dahlstar Orange' differed in leaf color as plants of 'Dahlstar Orange' had lighter green-colored leaves.
2. Plants of the new *Dahlia* and 'Dahlstar Orange' differed in ray floret color as plants of 'Dahlstar Orange' had darker orange-colored ray florets.
3. Plants of the new *Dahlia* and 'Dahlstar Orange' differed in disc floret color as plants of 'Dahlstar Orange' had orange-colored disc florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Bkdapor' grown in a container.

The photograph on the second sheet is a close-up view of a typical flowering plant of 'Bkdapor'.

DETAILED BOTANICAL DESCRIPTION

The aforementioned photographs and the following observations and measurements describe plants grown during the winter in 12-cm containers in a glass-covered greenhouse in Maasdijk, The Netherlands and under conditions and practices which approximate those generally used in commercial container *Dahlia* production. During the production of the plants, day and night temperatures ranged from 17° C. to 19° C. Plants were pinched one time and were three months old when the photographs and description were taken. In the following description, color references are made to The Royal Horticultural Society Colour Chart, 2007 Edition, except where general terms of ordinary dictionary significance are used.

Botanical classification: *Dahlia hybrida* 'Bkdapor'.

Parentage:

*Female, or seed, parent*.—Proprietary selection of *Dahlia hybrida* identified as code number 2006-1000, not patented.

*Male, or pollen, parent*.—Unknown selection of *Dahlia hybrida*, not patented.

Propagation:

*Type*.—By cuttings.

*Time to initiate roots, summer*.—About 16 days at temperatures of about 18° C. to 21° C.

*Time to initiate roots, winter*.—About 19 days at temperatures of about 18° C. to 21° C.

*Time to produce a rooted young plant, summer*.—About 21 days at temperatures of about 18° C. to 21° C.

*Time to produce a rooted young plant, winter*.—About 23 days at temperatures of about 18° C. to 21° C.

*Root description*.—Medium in thickness, fibrous, white in color; tuber development has not been observed.

*Rooting habit*.—Moderate branching; medium density.

Plant description:

*Plant form and growth habit*.—Compact, upright, somewhat outwardly spreading and mounding plant form; broad inverted triangle; two primary lateral branches develop, each primary lateral branch with numerous secondary branches; inflorescences held above the foliar plane on strong peduncles; bushy and dense growth habit.

*Plant height*.—About 13.4 cm.

*Plant diameter or spread*.—About 19.4 cm.

*Lateral branches*.—Length: About 6.3 cm. Diameter: About 5 mm. Internode length: About 8 mm. Aspect: About 30° from vertical. Strength: Strong. Texture: Smooth, glabrous. Color: Close to 187A to 187B.

Foliage description:

*Arrangement*.—Leaves opposite; leaves may be single or occasionally compound with three leaflets.

*Leaf length*.—About 7.5 cm.

*Leaf width*.—About 8.4 cm.

*Leaflet length*.—About 6.3 cm.

*Leaflet width*.—About 4.8 cm.

*Leaflet shape*.—Broadly ovate.

*Leaflet apex*.—Acuminate to acute.

*Leaflet base*.—Attenuate.

*Leaflet margin*.—Dentate to coarsely dentate.

*Leaflet venation pattern*.—Pinnate.

*Leaflet texture, upper and lower surfaces*.—Smooth, glabrous.

*Leaflet color*.—Developing leaves, upper surface: Close to 137A. Developing leaves, lower surface: Close to 138A to 138B. Fully expanded leaves, upper surface: Close to N137B; venation, close to 146A to 146B. Fully expanded leaves, lower surface: Close to 191A to 191B; venation, close to 146A.

*Petioles*.—Length: About 2.4 cm. Diameter: About 2.5 mm. Texture, upper and lower surfaces: Smooth, glabrous. Color, upper surface: Close to N199B tinged with close to 146A. Color, lower surface: Close to 146A.

Inflorescence description:

*Appearance and arrangement*.—Semi-double inflorescence form with ray and disc florets forming acropetally on a receptacle; inflorescences positioned above the foliar plane on strong peduncles; inflorescences face upright to slightly outwardly; freely flowering habit, about 18 inflorescences per plant.

*Fragrance*.—Faintly fragrant, sweet.

*Time to flower*.—Early flowering habit, plants begin flowering about 54 days after planting; plants flower continuously during the late summer in The Netherlands.

*Post-production longevity*.—Inflorescences maintain good substance for about two to three weeks on the plant; inflorescences not persistent.

*Inflorescence bud*.—Height: About 6 mm. Diameter: About 8 mm. Shape: Globular, flattened. Color: Close to 151B; towards the base, close to 152B.

*Inflorescence size*.—Diameter: About 5.5 cm. Depth (height): About 2.4 cm. Disc diameter: About 1.4 cm. Receptacle height: About 2 mm. Receptacle diameter: About 3 mm. Receptacle color: Close to 144B.

*Ray florets*.—Quantity per inflorescence: About 56 arranged in about four whorls. Length: About 2.5 cm. Width: About 9.5 mm. Shape: Obovate. Apex: Broadly acute. Base: Cuneate. Margin: Entire. Aspect: About 80° from vertical; ray florets concave. Texture, upper and lower surfaces: Smooth, glabrous. Color: When opening, upper surface: Close to N25C; towards the base, close to 42A and 44A. When opening, lower surface: Close to 24B; towards the base, close to 46A. Fully opened, upper surface: Close to 21C; towards the base, close to 42A; color does not change with development. Fully opened, lower surface: Close to 22B; color does not change with development.

*Disc florets*.—Quantity per inflorescence: About 40. Length: About 9 mm. Diameter: About 3 mm. Shape: Tubular, elongated; apices, acute. Texture, inner and outer surfaces: Smooth, glabrous. Color, when opening and fully opened: Close to 53A; towards the base, close to 150D.

*Phyllaries*.—Quantity per inflorescence: About twelve arranged in a single whorl. Length: About 9 mm. Width: About 3.5 mm. Shape: Oblong. Apex: Obtuse. Base: Broadly cuneate. Margin: Entire. Texture, upper and lower surfaces: Smooth, glabrous. Color, upper and lower surfaces: Close to 145A to 145B; towards the base, close to 144A.

*Peduncles*.—Length: About 5.4 cm. Diameter: About 2 mm. Aspect: Erect to about 30° from vertical.

Strength: Strong. Texture: Smooth, glabrous. Color: Close to N199A tinged with close to 152A.

*Reproductive organs*.—Androecium, present on disc florets only: Quantity per floret: About five. Filament length: About 4 mm. Filament color: Close to 1C. Anther shape: Narrowly oblong. Anther length: About 2 mm. Anther color: Close to 13A. Pollen amount: Scarce. Pollen color: Close to 13A. Gynoecium, present on ray and disc florets: Quantity per floret: One. Pistil length: About 9 mm. Style length: About 6 mm. Style color: Close to 154A to 154B. Stigma shape: Cleft. Stigma color: Close to 13A. Ovary color: Close to 145B. Seeds/fruits: Seed and fruit development have not been observed on plants of the new *Dahlia*.

Disease/pest resistance: Plants of the new *Dahlia* have not been shown to be resistant to pathogens and pests common to *Dahlia*.

Garden performance: Plants of the new *Dahlia* have been observed to have good garden performance and to tolerate wind and rain. Plants of the new *Dahlia* have been observed to be tolerant to high temperatures of 35° C. and hardy to USDA Hardiness Zone 8.

It is claimed:

1. A new and distinct *Dahlia* plant named 'Bkdapor' as illustrated and described.

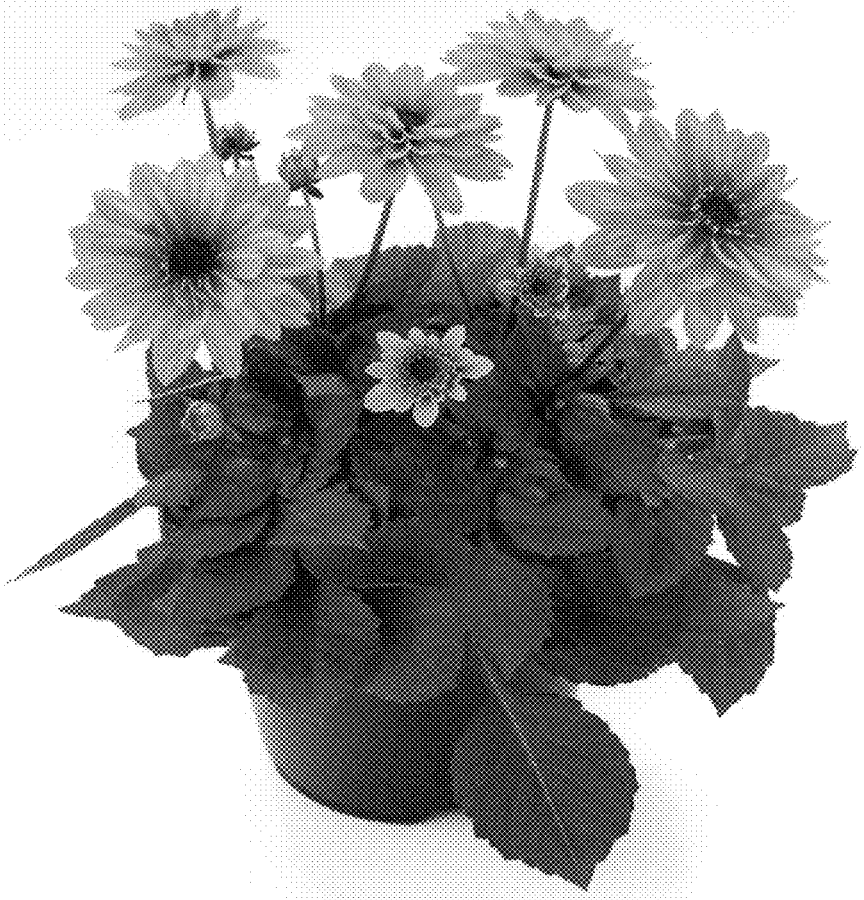

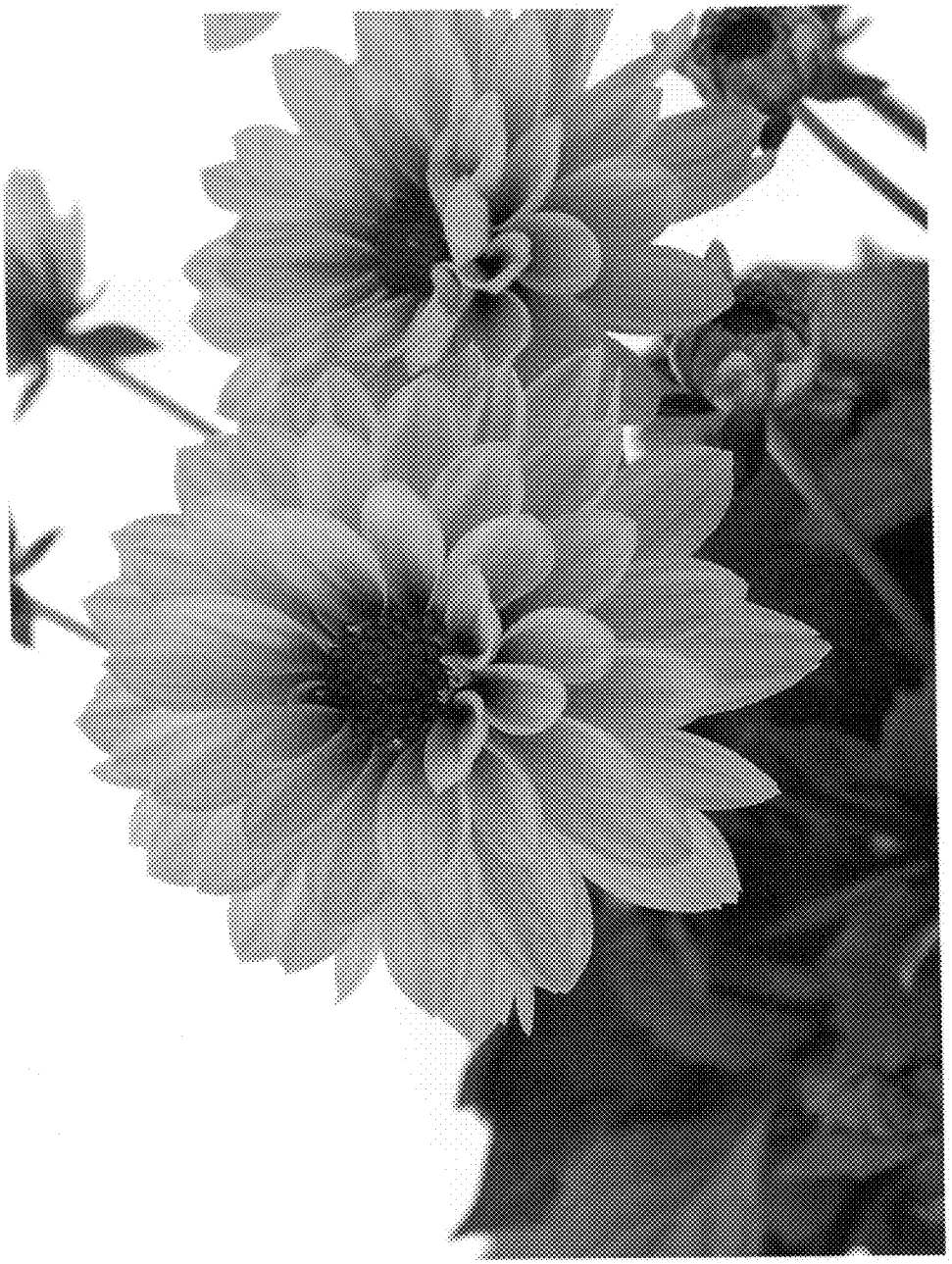

* * * * *